United States Patent
McAndrew et al.

[11] Patent Number: 6,084,668
[45] Date of Patent: Jul. 4, 2000

[54] IN-LINE CELL FOR ABSORPTION SPECTROSCOPY

[75] Inventors: James J.F. McAndrew, Lockport; Ronald S. Inman, Lyons, both of Ill.

[73] Assignee: American Air Liquide Inc., Walnut Creek, Calif.

[21] Appl. No.: 09/114,760

[22] Filed: Jul. 13, 1998

Related U.S. Application Data

[63] Continuation-in-part of application No. 08/890,928, Jul. 10, 1997, Pat. No. 5,949,537.

[51] Int. Cl.[7] ........................................... G01N 1/10

[52] U.S. Cl. ................................................. 356/246

[58] Field of Search ............................. 356/244, 246, 356/236, 432–444; 250/343, 573, 576, 353; 359/850, 858, 861

[56] References Cited

U.S. PATENT DOCUMENTS

| | | | |
|---|---|---|---|
| 4,990,780 | 2/1991 | Lee et al. | 250/343 |
| 5,949,537 | 9/1999 | Inman et al. | 356/246 |

FOREIGN PATENT DOCUMENTS

| | | |
|---|---|---|
| 0015170 | 9/1980 | European Pat. Off. . |
| 0 456 202 | 11/1991 | European Pat. Off. . |
| 0 596 605 | 5/1994 | European Pat. Off. . |
| 0647845 | 4/1995 | European Pat. Off. . |
| 0 706 042 | 4/1996 | European Pat. Off. . |
| 0 768 525 | 10/1996 | European Pat. Off. . |
| 0 768 521 | 4/1997 | European Pat. Off. . |
| 3633931 | 4/1988 | Germany . |
| 4214840 | 11/1993 | Germany . |
| 2075213 | 11/1981 | United Kingdom . |
| 2165640 | 4/1986 | United Kingdom . |
| WO90/00732 | 1/1990 | WIPO . |

OTHER PUBLICATIONS

White, "Long Optical Paths of Large Aperture," J. Opt. Soc. Am., vol. 32 (1942), pp. 285–288.

T.A. HU et al, "Improved Multipass Optics for Diode Laser Spectroscopy," Review of Scientific Instruments, vol. 64, No. 12, Dec. 1993, pp. 3380–3383.

Patent Abstracts of Japan, vol. 6, No. 59, JP 57–1953, Jan. 1982.

Fried et al, "Versatile Integrated Tunable Diode Laser System for High Precision: Application for Ambient Measurements of OCS," Applied Optics, vol. 30, No. 15, May 20, 1991, pp. 1916–1932.

May, "Correlation–Based Technique for Automated Tunable Diode Laser Scan Stabilization," Rev. Sci. Instrum., vol. 63, No. 5, May 1992, pp. 2922–2926.

Eng et al., "Tunable Diode Laser Spectroscopy: An Invited Review," Optical Engineering, Nov./Dec. 1980, vol. 19, No. 6, pp. 945–960.

Lundqvist et al, "Measurements of Pressure–Broadening Coefficients of NO and $O_3$ Using a Computerized Tunable Diode Laser Spectrometer," Applied Optics, vol. 21, No. 17, Sep. 1, 1982, pp. 3109–3113.

(List continued on next page.)

*Primary Examiner*—Frank G. Font
*Assistant Examiner*—Michael P. Stafira
*Attorney, Agent, or Firm*—Burns, Doane, Swecker & Mathis, L.L.P.

[57] ABSTRACT

Provided is a novel in-line cell useful in absorption spectroscopy. The cell includes a sample region, a light entry port and a light exit port being the same or separate ports. Each port is in communication with the sample region and contains a light transmissive window. A mirror having a light reflective surface faces the sample region, and a heater effective to heat the light transmissive window in the light entry port and/or said light exit port is provided. The cell can be used to determine the concentration of molecular gas impurities in a sample. Particular applicability is found in semiconductor manufacturing in a semiconductor processing tool.

18 Claims, 7 Drawing Sheets

OTHER PUBLICATIONS

Ahlberg et al, "IR–Laser Spectroscopy for Measurement Applications in the Industrial Environment," TR 85170, Dec. 85.

HÖJER et al, "Measurements of Electric Field Strength in Gas Insulated High–Voltage Components Using Infrared Diode Laser Absorption Spectroscopy," Applied Optics, vol. 25, No. 17, Sep. 1, 1986; pp. 2984–2987.

Cassidy, "Trace Gas Detection Using 1.3 µm InGaAsP Diode Laser Transmitter Modules," Applied Optics, vol. 27, No. 3, Feb. 1, 1988, pp. 610–614.

Mitsui et al, "Development of New APIMS for the Detection of Trace Impurities in Special Gases," Proceedings of the 40th Annual Technical Meeting of the IES, Chicago, pp. 246–253 (1994).

Herriott et al, "Folded Optical Delay Lines," Applied Optics, vol. 4, No. 8, pp. 883–889 (Aug. 1965).

Schaeffer et al, "Multipass absorption cell designed for high temperature UHV operation," Applied Optics, vol. 28, No. 9, May 1989.

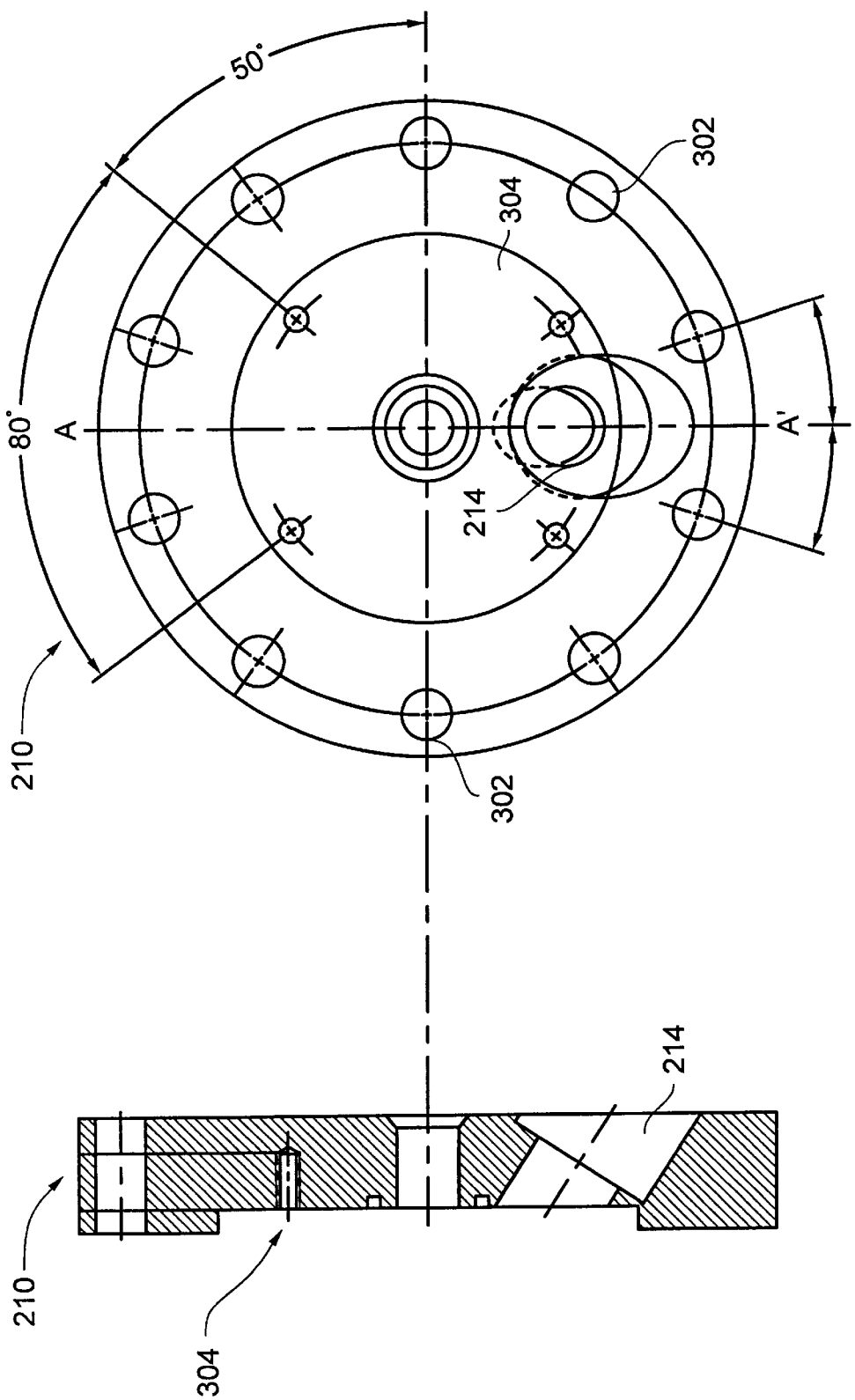

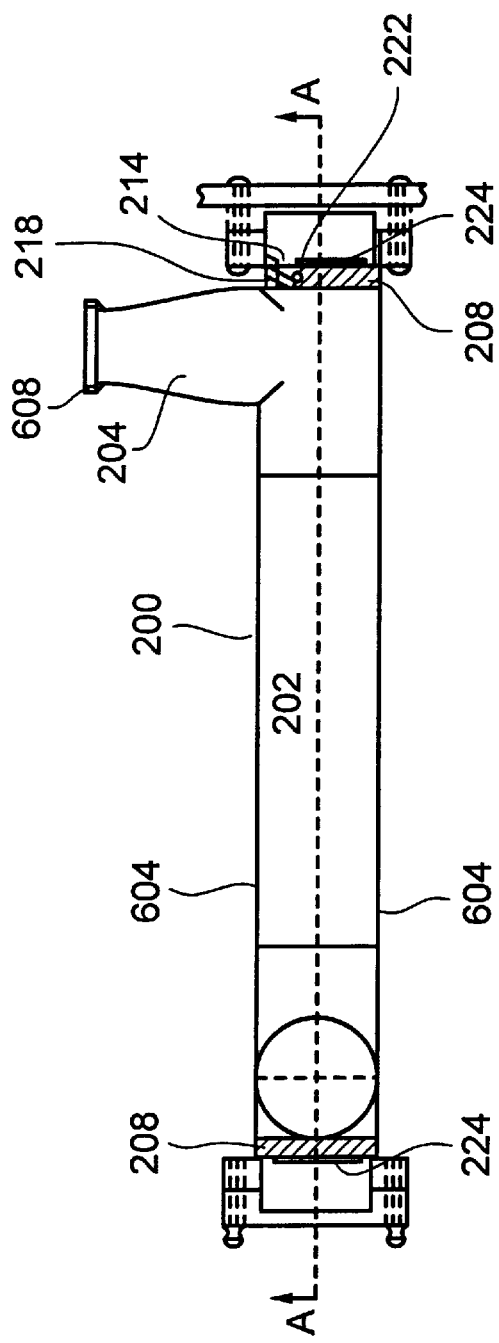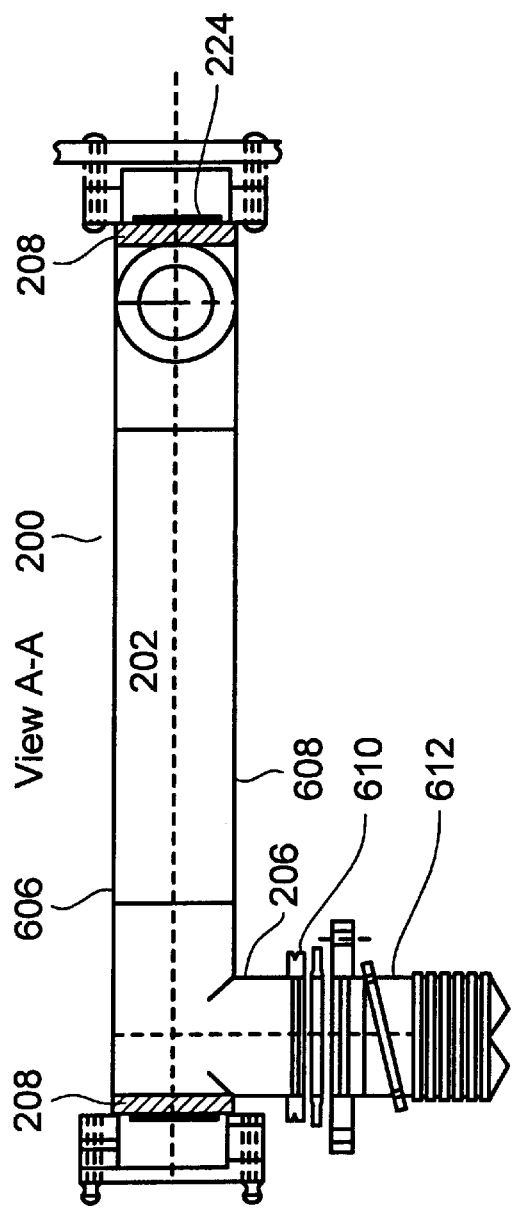

IN-LINE CELL FOR ABSORPTION SPECTROSCOPY

CROSS REFERENCE TO RELATED APPLICATIONS

This application is a Continuation-in-Part of application Ser. No. 08/890,928 filed Jul. 10, 1997, now U.S. Pat. No. 5,949,537 the content of which is herein incorporated by reference.

BACKGROUND OF THE INVENTION

1. Field of the Invention

The present invention relates to a novel in-line cell useful in absorption spectroscopy. The present invention also relates to a system for performing an absorption spectroscopy measurement in a sample and to a semiconductor processing apparatus which comprise the novel in-line cell.

2. Description of the Related Art

Semiconductor integrated circuits (ICs) are manufactured by a series of processes, many of which involve the use of gaseous materials. Included among such processes are etching, diffusion, chemical vapor deposition (CVD), ion implantation, sputtering and rapid thermal processing.

Many of the gases used in these processes are highly reactive and tend to form deposits on surfaces with which they come into contact, especially under conditions used in IC fabrication, such as high temperature or plasma conditions. When an in-line spectroscopic sensor is used to monitor a process in such aggressive atmospheres, deposits from the process gases tend to form on various surfaces, for example, the optical surfaces, of the sensor. As a result, sensor performance tends to deteriorate.

The sensitivity of detection of gas phase molecular species by absorption spectroscopy increases as the length of the light path through the sample increases, for constant pressure and concentration. The intensity of light reaching the detector is given by Beer's Law as follows:

$$I = I_o \cdot e^{-\alpha c l}$$

where $I_o$ is the intensity of the incident radiation, $\alpha$ is the absorptivity, $l$ is the pathlength through the sample, $c$ is the concentration of the impurity in the sample (by volume), and P is the total pressure of the sample. For small absorptions, the amount of light absorbed is given by $$I - I_o = \alpha c l$$

In order to make $l$ large, it is frequently impractical to place the light source and detector very far apart and so "folded" light paths are often used, in which mirrors reflect the light back and forth through the sample gas many times.

The Herriott design is often preferred for tunable diode laser absorption spectroscopy (TDLAS). As shown in FIG. 1, the Herriott cell 100 uses two curved mirrors 102 mounted at opposite ends of a usually cylindrical gas sample cell 104. Simple multi-pass arrangements are often used, such as described in U.S. Pat. No. 3,524,066, to Blakkan, and U.S. Pat. No. 5,173,749, to Tell et al, the contents of which are herein incorporated by reference. A planar polygonal multipass cell is described by the present inventors in copending application Ser. No. 08/711,504, filed Sep. 10, 1996 now U.S. Pat. No. 5,818,578, the contents of which are herein incorporated by reference.

In the multipass cells described above, deposits formed on optical components thereof can adversely impact on the sensitivity and operation of the sensor. For example, deposits formed on the reflective surfaces of the mirrors can reduce their reflectivity and hence the light intensity which reaches the detector after multiple reflections of the light beam. Likewise, the formation of deposits on the light transmissive window(s), through which the light beam enters and exits the measurement cell, acts to reduce the light intensity reaching the detector. Such reduction in light intensity reduces the measurement sensitivity and may eventually lead to a condition in which the sensor does not function at all.

Deposits on the mirrors and light transmissive windows can be removed by disassembling the sensor and mechanically cleaning the contaminated components. Such maintenance, however, is inconvenient and expensive. Avoidance thereof is, therefore, desirable.

The use of a purge gas to minimize deposits on optical surfaces in an in-situ particle monitor has been described in U.S. Pat. No. 5,360,980, to Borden. As disclosed therein the purge gas flow should be large compared with the total process gas flow. This requires that the vacuum pump used to evacuate the process chamber be increased in size. Such requirement is both expensive and impractical.

To meet the requirements of the semiconductor processing industry and to overcome the disadvantages of the related art, it is an object of the present invention to provide a novel in-line cell useful in absorption spectroscopy. The in-line cell allows for accurate, in-situ absorption spectroscopy measurements which can be used, for example, to accurately and sensitively measure the concentration of gas phase molecular impurities in a sample. The problems associated with the formation of deposits on optical surfaces of the cell, such as the reflective surfaces of mirrors and the light transmissive window surfaces within the measurement cell can be avoided or conspicuously ameliorated by the inventive cell.

It is a further object of the present invention to provide an absorption spectroscopy system which includes the inventive in-line cell.

It is further an object of the present invention to provide a semiconductor processing apparatus which includes the absorption spectroscopy system for performing in-situ measurements.

Other objects and aspects of the present invention will become apparent to one of ordinary skill in the art on a review of the specification, drawings and claims appended hereto.

SUMMARY OF THE INVENTION

According to a first aspect of the present invention, a novel in-line cell useful in absorption spectroscopy is provided. The in-line cell includes a sample region, a light entry port and a light exit port. The light entry port and light exit port can be the same or separate ports. Each port is in communication with the sample region and contains a light transmissive window. A mirror having a light reflective surface faces the sample region, and a heater effective to heat the light transmissive window in the light entry port and/or light exit port is provided.

The in-line cell allows for accurate, in-situ absorption spectroscopy measurements which are useful, for example, to accurately and sensitively measure the concentration of gas phase molecular impurities, such as, e.g., methane, moisture (water vapor) and carbon dioxide, in a sample. By heating optical components of the cell, for example, light transmissive window(s) and mirrors, the critical surfaces thereof can be maintained in a deposit-free state.

According to a further aspect of the invention, a system for performing an absorption spectroscopy measurement is provided. The system includes an in-line cell as described above with reference to the first aspect of the invention. The inventive system further comprises a light source for generating a light beam which passes through the light entry port into the cell, and a main detector for measuring the light beam exiting the cell through the light exit port.

According to a third aspect of the invention, a semiconductor processing apparatus is provided. The apparatus comprises a processing chamber in communication with a means for evacuating the chamber, and the inventive absorption spectroscopy measurement system described above.

BRIEF DESCRIPTION OF THE DRAWINGS

The objects and advantages of the invention will become apparent from the following detailed description of the preferred embodiments thereof in connection with the accompanying drawings, in which like reference numerals denote like features, and in which:

FIGS. 3A and 3B are cross-sectional and top plan views, respectively, of a flange which forms a portion of the in-line cell in accordance with the invention;

FIGS. 6A and 6B are top plan and side-sectional views, respectively, of an in-line cell in accordance with a further aspect of the invention;

DETAILED DESCRIPTION OF THE PREFERRED EMBODIMENTS OF THE INVENTION

Figure 1:
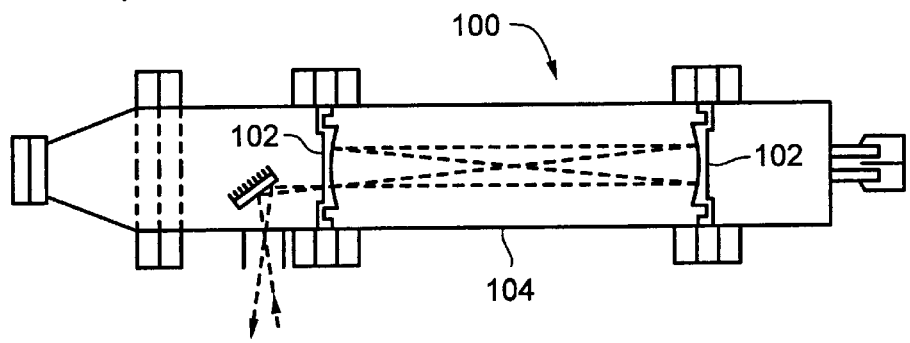
FIG. 1 is a conventional absorption spectroscopy cell according to the Herriott design.
Figure 2:
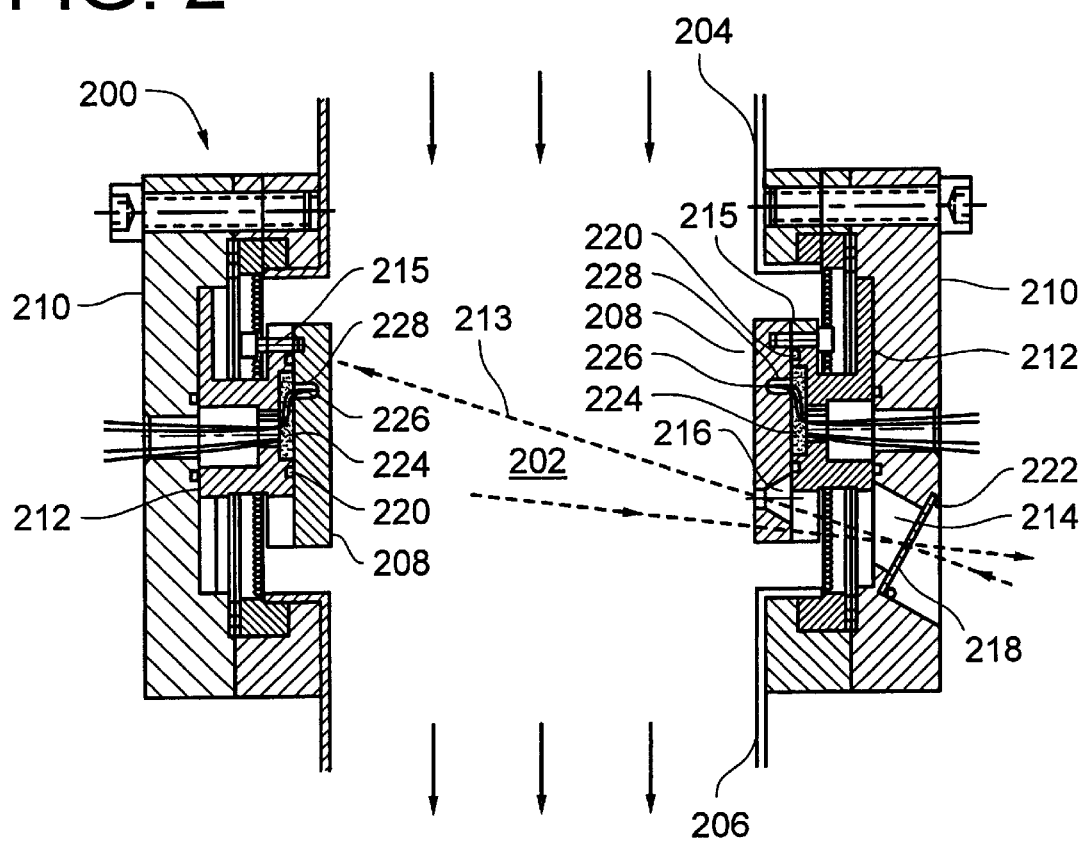
FIG. 2 is a cross-sectional view of an in-line cell in accordance with one aspect of the invention.

FIG. 2 illustrates a cross-sectional view of an exemplary in-line cell 200 useful in absorption spectroscopy according to one aspect of the invention. While the exemplary cell is of the Herriott type of multipass cell, it should be clear that the inventive concepts described hereinbelow are in no way limited thereto, and can readily be applied to other forms of cells.

The in-line cell 200 includes a sample region 202. The walls of the cell preferably define a substantially cylindrical space through which the sample gas flows. The sample gas flows through the cell from a sample inlet port 204 into sample region 202, and out of the cell through exhaust port 206.

The inlet port 204 is to be connected to a source of the sample to be measured. As later described, inlet port 204 can advantageously be connected to an exhaust line from a semiconductor processing tool in order to perform in-situ measurements. In this way, concentrations of molecular gas species in the processing tool exhaust can be measured. The exhaust port 206 is typically connected to the foreline of a vacuum pump or other exhausting means, for example a fan or blower. Connection of the inlet and exhaust ports with the sample source and the exhausting means, respectively, can be made using known means, such as with flanges and flexible hoses.

A plurality of preferably curved mirrors 208 are disposed along the interior of the cell, and are each fixed to a flange 210 by a mirror bracket 212 using fasteners 215. It is noted that the flange and mirror structures will vary depending on whether they function as part of a light beam entry/exit structure. Each of the mirrors has a light reflective surface facing the sample region, and is disposed such that a light beam 213 entering the cell is reflected from one mirror to another through the sample region until each mirror has reflected the light beam at least one time prior to exiting the cell.

The light reflective surfaces are preferably a polished metal. As a high reflectivity of these surfaces is desirable, the surfaces can be coated with one or more layers of a reflective material such as gold, other metallic layers or a highly reflective dielectric coating, in order to enhance the reflectivity thereof.

The cell further includes a light entry and exit port 214 in flange 210, for allowing a light beam to pass into and out of the cell. As illustrated, mirror 208 includes an aperture 216 extending therethrough, through which the light beam can pass. While the exemplary embodiment shows a single port through which the light beam enters and exits the cell, a plural port structure is also envisioned. Thus, the light beam can enter and exit the cell through the same or different ports in the cell, and can enter and/or exit the cell through plural light entry or light exit ports. Further, the ports can be disposed on the same side or different sides of the cell.

The light entry/exit port 214 contains a light transmissive window 218 which allows the light beam to pass into and out of the cell and through the sample region. Suitable light transmissive materials for the window are known and include, for example, aluminum oxide, quartz and magnesium fluoride.

Light transmissive window 218 can additionally be provided with a coating layer on a surface opposite the surface facing the sample region for reflecting a portion of the light beam. Subtracting the signal due to the reflected portion of the beam from that of the transmitted portion can result in more accurate absorption measurements than otherwise possible. Among the commercially available coating materials, metallic coatings are preferred.

As shown in the exemplified embodiment, light transmissive window 218 is preferably offset at an angle from perpendicular relative to the incoming light beam. While the Brewster angle is a preferred offset angle for its effectiveness, angles smaller than the Brewster angle are typically more convenient and are also effective. By offsetting the window in this manner, coherent interference caused by the reflected portion of the beam can be avoided. As a result, measurement of greater accuracy can be obtained. Such an offset can further serve the same purpose as that served by the optional coating layer described above. That is, the reflected portion of the beam can be used to obtain a more accurate measurement by subtracting out the signal due to background noise.

The cell 200 should be sealed in a substantially airtight manner, to makes possible the measurement of gas samples at lower than atmospheric pressures, i.e., at vacuum conditions. As a result, in-situ measurements in vacuum processing tools such as used in the semiconductor manufacturing industry can effectively be performed. To ensure that the measurement cell remains airtight, an o-ring 220 or some other type of vacuum seal known to those skilled in the art can be employed to seal mirror 208.

To minimize or prevent deposits from being formed on the surface of the windows exposed to the gas being sampled, one or more window heaters 222 are provided. The heater should be capable of raising the window to a temperature of from about 50 to 150° C., preferably from about 100 to 150° C., although optimal temperatures are process dependent. In the exemplified embodiment, the heater is disposed in contact with the window at the periphery thereof.

Suitable heaters include, but are not limited to, resistance-type heaters, self-regulating-type heaters such as heat trace, heating lamps, inductive heaters and liquid or gaseous heating fluids which optionally can be circulated. Of these, resistance-type heaters are preferred.

The window itself, or any window mount which provides sufficient heat conduction and makes good thermal contact with the window, can be brought into direct physical (and thermal) contact with a heating element or, as in the case with lamp-type heaters, into direct thermal contact with the heating element located outside the cell. Generally, as long as the thermal resistance of the path from the heater to the window surface is less than the thermal resistance of the heat path to other surfaces inside the sample cell (or any nearby region), then the desired results can be achieved.

In addition to the heating of the windows, mirrors 208 can additionally or alternatively be heated in order to minimize or eliminate the formation of deposits on the light reflective surfaces thereof. The mirror heaters 224 should be capable of raising the light reflective surfaces to an effective temperature to prevent the formation of deposits thereon. The temperature ranges contemplated for the light transmissive window are also applicable to the mirrors. The heating means outlined above with respect to the windows are also applicable to the mirror heater. As with the window heater, thermal resistance of the path from the mirror heater 224 to the mirror should be less than the thermal resistance of the heat path to other surfaces in the cell.

A temperature sensor 226, for example, a thermistor, is provided for monitoring the temperature of the mirror. As shown, the temperature sensor is preferably disposed in a hole 228 extending partially through the mirror in order to obtain an accurate measurement.

In the exemplified cell, mirror 208 is heated using a different heater 224 than that 222 used to heat the window. However, depending on the window/heater design, use of a single heater is possible. Furthermore, a purge gas stream as described above with reference to the window can also be applied to the mirror.

The cell is constructed in such a fashion that the windows and/or mirrors can be maintained at a temperature higher than that of nearby surfaces in the cell which are exposed to the atmosphere to be analyzed. Since the deposits tend to form on lower temperature surfaces, deposits can be effectively prevented from forming on the heated window mirror surface facing the sample region.

Heating of the cell's optical elements as described above should be contrasted with the situation in which the entire cell is heated. In such a case, heat transfer from the body of the cell to the windows and mirrors is not facilitated. Consequently, the windows and mirrors would tend to be at a lower temperature than the walls of the cell, resulting in deposits being concentrated on the mirrors.

The objectives of the invention can be achieved by disposing the heaters outside of the area of the cell exposed to the sample gas. This allows heat to be directly applied to the back-surface of the optical components. In this manner, it is possible to attain the objective of maintaining the critical surfaces of the optical components at a higher temperature than other surfaces in the cell, while at the same time, isolating the heaters from the aggressive environment in the sample region. This is especially desirable since placement of the heater directly in the sample region would result in corrosion or other damage to the heater.

In addition to the above-described window and mirror heaters, a purge gas flow can optionally be introduced into the cell to further prevent the accumulation of deposits on the windows and/or light reflective surfaces of the mirrors. This can result in an enhancement of the effect of heating to further reduce deposition. Suitable purge gases include an inert gas, such as nitrogen, argon or helium. If the purge gas is heated, it can serve the purpose of the window or mirror heater described above. Preferably, such heated gas is localized on the window or light reflective surface of the mirror. Therefore, such a heated purge gas stream can be used by itself or together with other types of heaters such as described above, to effectively prevent deposits on the optical component critical surfaces.

For an unheated purge gas stream, it is preferable to localize the flow of the gas in the vicinity of the critical surface. By minimizing the flow of the purge gas, the need for retrofitting vacuum systems with larger capacity pumps can be eliminated.

FIG. 3B illustrates a top plan view of a flange 210 which incorporates a light entry/exit port 214, and FIG. 3A is a cross-sectional view taken along line A–A' of FIG. 3B. In addition to the features discussed above, a plurality of fastener holes 302 are provided through flange 210 to allow the flange to be secured to the body of the cell. The flange further has a recessed portion 304, which is adapted to receive a mirror bracket (not shown).

Figure 4C:
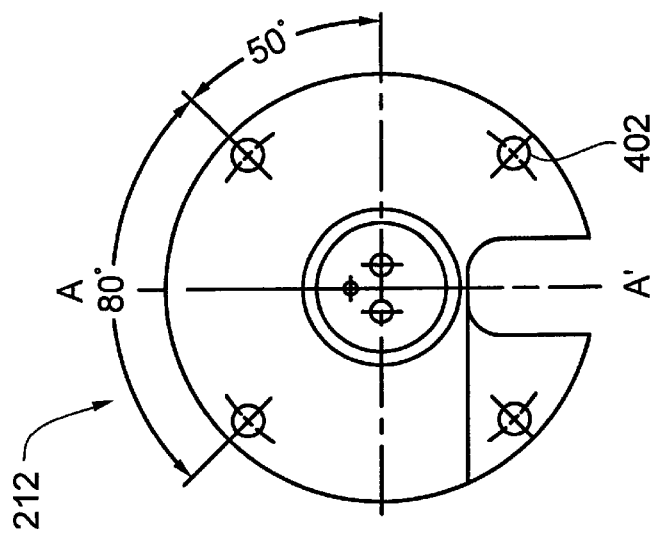
FIGS. 4A, 4B and 4C are top plan, cross-sectional and bottom plan views, respectively, of a mirror bracket which forms a portion of the in-line cell in accordance with the invention.
Figure 4B:
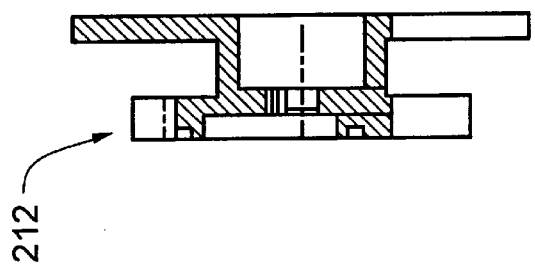
Figure 4A:
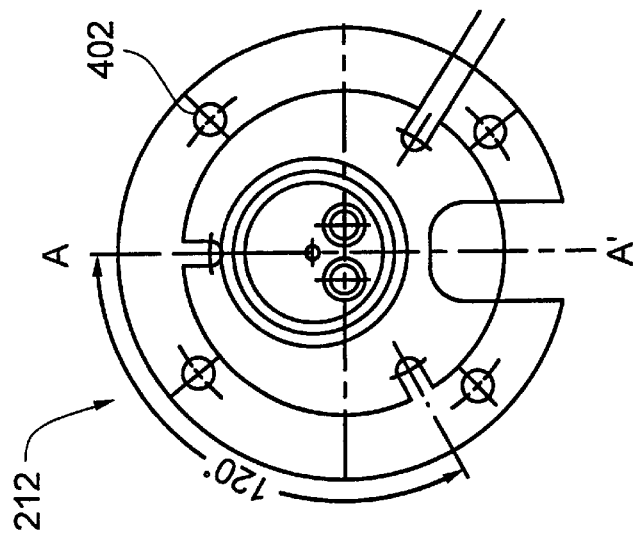

FIGS. 4A, 4B and 4C are top plan, cross-sectional and bottom plan views, respectively, of mirror bracket 212. The cross-section of FIG. 4B is taken along line A–A' of FIGS. 4A and 4C. As described above, it is the function of mirror bracket 212 to secure the light reflective mirror to the flange. Fastener holes 402 in the mirror bracket allow mirror 208 to become secured thereto by use of suitable fasteners.

Figure 5A:
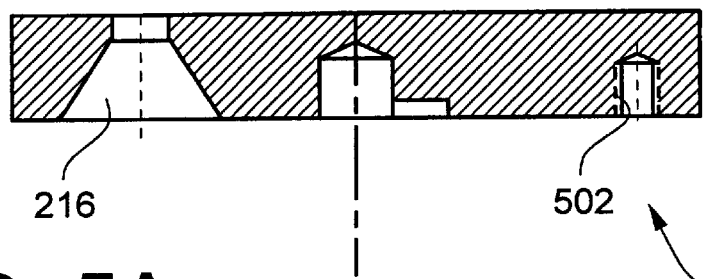
FIGS. 5A and 5B are top plan and cross-sectional views, respectively, of a mirror which forms a portion of the in-line cell in accordance with the invention.
Figure 5B:
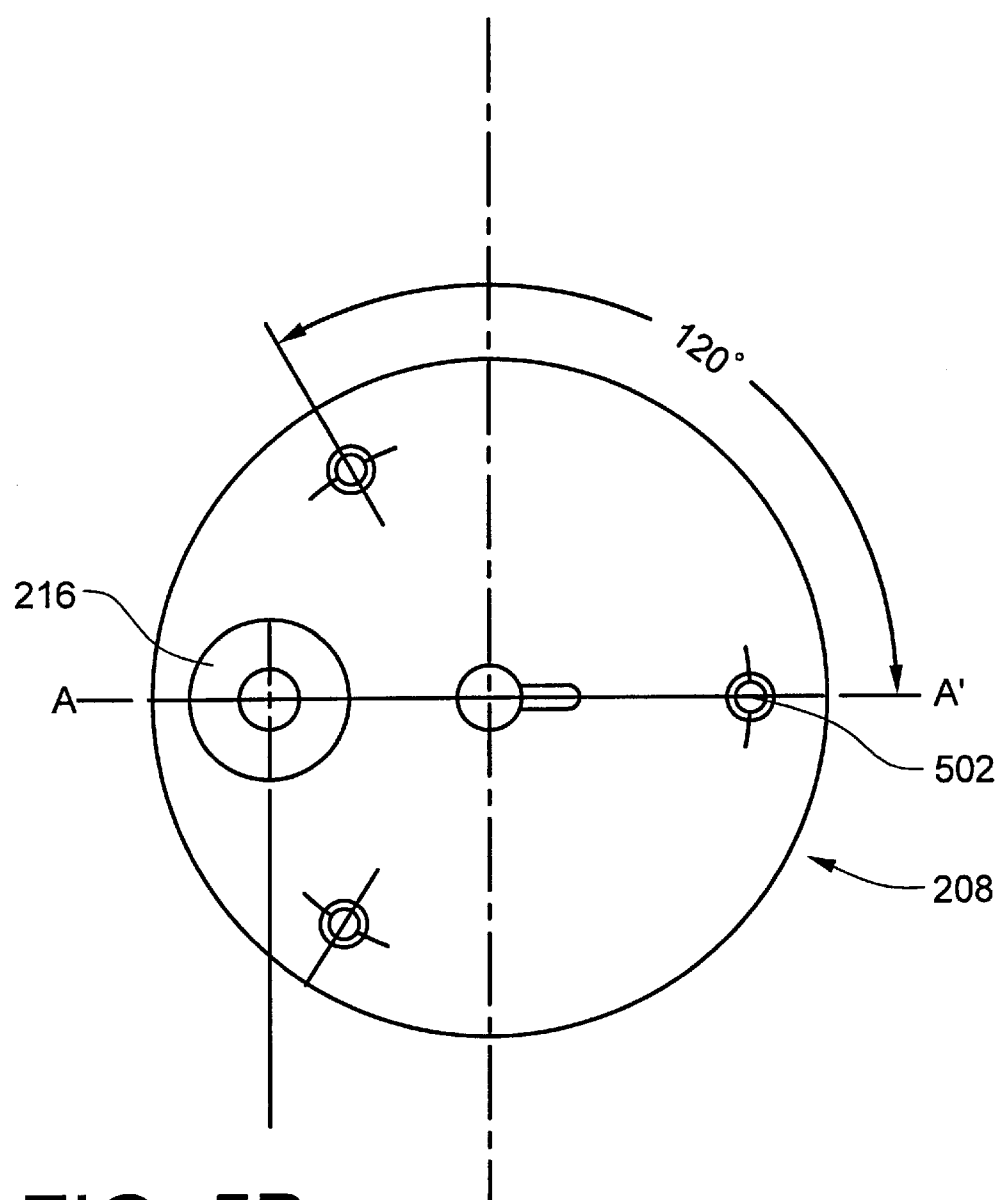

An exemplary mirror 208 in accordance with the invention is shown in FIGS. 5A and 5B. FIG. 5B is a cross-sectional view taken along line A–A' of FIG. 5A. As previously discussed, mirror 208 includes a light beam aperture 216 extending therethrough, through which the light beam can pass into and out of the measurement cell. As illustrated, aperture 216 is preferably tapered to provide a clear path for the light beam, which enters and exits the cell at different angles. Fastener holes 502 are provided to allow the mirror to be secured to the flange 200 with suitable fasteners. In addition, while the illustrated mirror appears planar, mirror 208 is preferably curved.

FIG. 6A illustrates a top plan view of an in-line cell useful in absorption spectroscopy according to a further aspect of the invention, and FIG. 6B shows a side-sectional view taken along line A—A of FIG. 6A. The description above with respect to the in-line cell of FIG. 2 is generally applicable to the in-line cell of FIGS. 6A and 6B, with the following additional comments.

Unlike the previously described cell, the cell shown in FIGS. 6A and 6B results in a non-parallel flow of gas through the cell from the sample inlet port 204, into sample region 202 and out of the cell through exhaust port 206. The in-line cell 200 includes a sample region 202, which is bounded by sidewalls 604, top wall 606 and bottom wall 608. Mirrors 208 are disposed at opposite ends of the cell, with light reflective surfaces thereof facing the sample region. As with the previously described cell, the cell interior is preferably cylindrical in shape, for ease of construction and performance under vacuum or process conditions. While illustrated in simplified form, the flange, mirror bracket, mirror and heater structures described above can be used in this cell. The inlet port 204 is connected to a sample source by flange 608, while exhaust port 206 can be connected to an exhaust line by way of flange 610 and flexible hose 612.

Although the exemplified in-line cells are of a Herriott design, the inventive concepts can readily be applied to other types of in-line cells. For example, the inventive concepts can be applied to polygonal multipass cells or to any form of cell which is amenable to the above conditions with respect to the mirror and heater structures.

The in-line cell should be constructed of materials which are compatible with the atmospheres being contained therein. Such materials are within the knowledge of persons skilled in the art. For example, various forms of stainless steel can be used for cell surfaces which contact the sample being measured.

Figure 7:
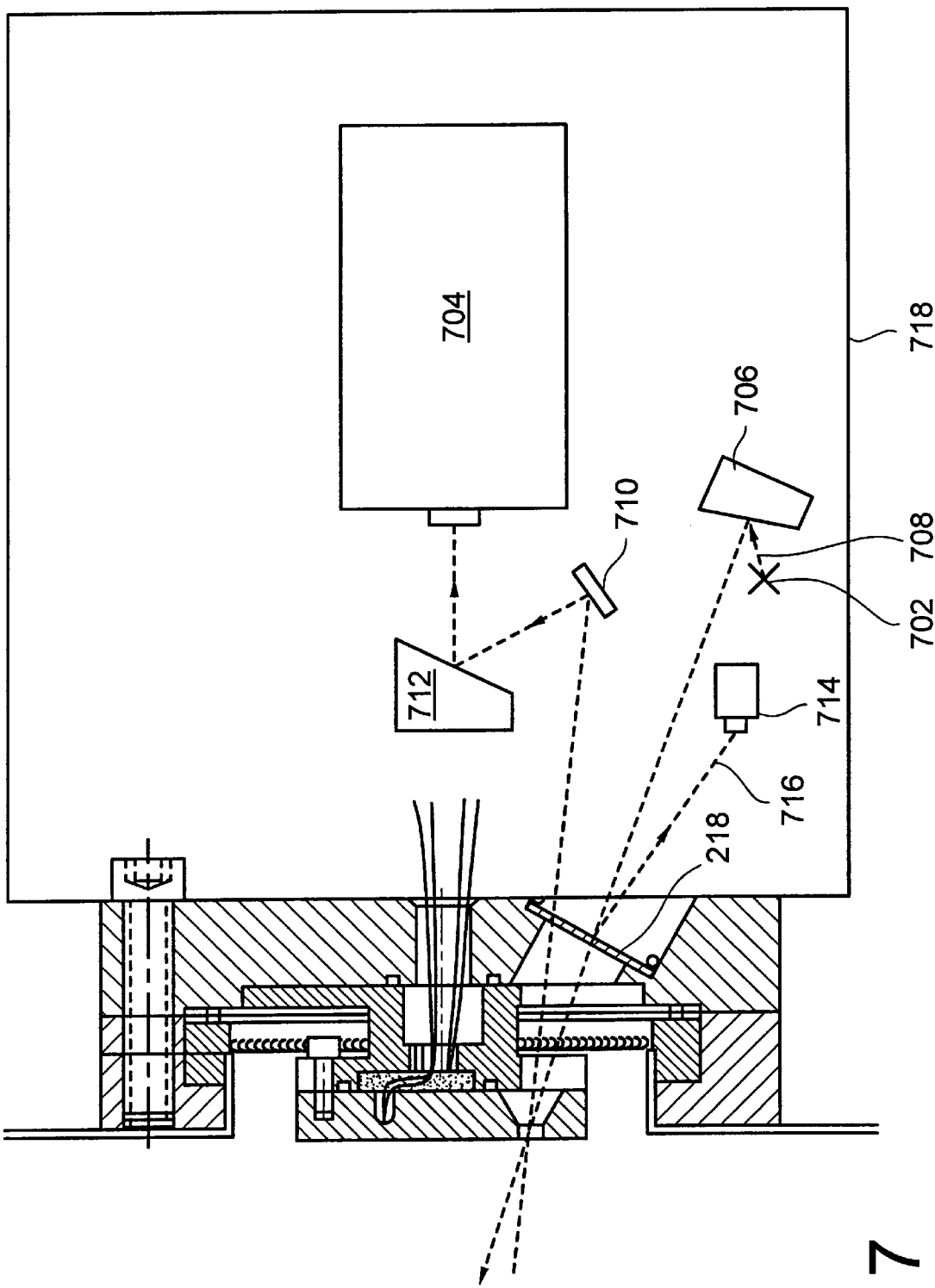
FIG. 7 is a top plan view of a light source/detector scheme in a system for performing an absorption spectroscopy measurement in accordance with the invention.

While the inventive cell can be used for any absorption spectroscopy technique, it is preferably used in tunable diode laser absorption spectroscopy (TDLAS). With reference to FIG. 7, such a system includes, in addition to the in-line cells described above, a light source 702, preferably a diode laser, for generating a light beam which is directed through the light transmissive window 218 into the sample region of the cell. To measure the light beam which exits the cell through the light transmissive window, the system further includes a main detector 704, which can be, for example, a photodiode.

Any molecular impurity of interest can be detected, subject only to the availability of a suitable light source. For example, water vapor, nitric oxide, carbon monoxide and methane or other hydrocarbons can be detected by measuring the attenuation of light from a diode laser source which emits light of a wavelength characteristic of the impurity.

Laser light sources which emit light in spectral regions where the molecules of interest absorb most strongly lead to improvements in measurement sensitivity. In particular, light sources which emit at wavelengths longer than about 2 $\mu$m are preferred, since many of the molecular impurities of interest have strong absorption bands in this region.

Any suitable wavelength-tunable light source can be used. Of the currently available light sources, diode laser light sources are preferred because of their narrow linewidth (less than about $10^{-3}$ cm$^{-1}$) and relatively high intensity (about 0.1 to several milliwatts) at the emission wavelength.

Examples of diode lasers include Pb-salt and GaAs-type diode lasers. The Pb-salt-type laser requires cryogenic temperatures for operation and emits infrared light (i.e., wavelength greater than 3 $\mu$m), while the GaAs-type diode laser can operate at close to room temperature and emits in the near infrared region (0.8–2 $\mu$m).

Recently, diode lasers which include Sb in addition to GaAs (or other pairs of III-V compounds such as AsP) have been described (see, "Mid-infrared wavelengths enhance trace gas sensing," R. Martinelli, Laser Focus World, March 1996, p. 77). These diodes emit light of a wavelength greater than 2 $\mu$m while operating at −87.8° C. While such a low temperature is not convenient, it compares favorably with the cryogenic temperatures (less than −170° C.) required by Pb-salt lasers.

Operation of similar lasers at 4 $\mu$m and 12° C. has also been reported (see, Lasers and Optronics, March 1996). Diode lasers of the above described type will most preferably operate at temperatures of at least −40° C. Use of a thermoelectric cooler for temperature control at such temperatures makes these light sources less complicated than the lower temperature diode systems.

To make use of these lasers more desirable, improvement in the optical properties over current levels is important. For example, single mode diodes (i.e., diodes whose emission at fixed temperature and drive current is at a single wavelength with emission at other wavelengths at least 40 dB less intense) should be available.

Suitable light sources for use in the invention are not limited to the above described diode lasers. For example, other types of lasers which are similarly sized and tunable by simple electrical means, such as fiber lasers and quantum cascade lasers, are envisioned. The use of such lasers as they become commercially available is envisioned.

The system can further include at least one mirror 706 for reflecting the light beam 708 from the light source 702 through the light transmissive window into the cell, and at least one additional mirror 710, 712 for reflecting the light beam exiting the cell to the main detector.

The mirror 706 is preferably curved in order to collimate the light beam as the light from the diode laser source is divergent. Alternatively, a lens may be used to collimate the diode laser output. If a lens is used, it should be anti-reflective (AR) coated to minimize reflection of light back into the laser, as this can cause undesirable laser noise. Suitable AR coatings are commercially available. Likewise, mirror 712 is preferably curved in order to focus the parallel light beam on the main detector.

A second detector 714, which can also be a photodiode, for measuring a portion of the light beam 716 which is reflected from the light transmissive window 218 as well as means for subtracting this reference signal from a measurement obtained by the main detector can optionally be provided in the system. An operational amplifier in a configuration such as described in the literature (See, e.g., Moore, J. H. et al "Building Scientific Apparatus", Addison Wesley, London, 1983) can act as the means for subtracting the reference signal. Alternatively, a canceller circuit can be used.

The reflected light does not show any absorption by the molecules of interest in the sample region, and therefore provides a reference signal. By subtracting the reference signal from that of the light which passes through the cell (which is measured by the main detector), variations in the light source can be compensated for. This also allows for enhanced sensitivity to signal changes due to molecules in the system chamber 718.

While "dual beam" techniques using subtraction of a reference beam are well-known they usually require a dedicated beam-splitter, i.e., an optical element whose only function is to divide the light beam. According to the present invention, the entrance window to the chamber can provide this function without the need for any additional components. The ratio of transmitted to reflected light at this window can be controlled by use of an appropriate coating for the window.

The inventive system has particular applicability in detecting a molecular species in a gas exhausted from a vacuum chamber. In such a case, the cell can be disposed in a vacuum exhaust line between a vacuum chamber and a vacuum pump system.

The system is compatible with a wide range of materials. For example, the vacuum chamber can contain certain reactive or nonreactive (inert) gas species which can be in a plasma- or non-plasma state. Examples of reactive gases which are compatible with the inventive system include $SiH_4$, HCl and $Cl_2$ provided the moisture level is less than 1000 ppm. Any inert gas such as, e.g., $O_2$, $N_2$, Ar and $H_2$ can be used in the inventive system. In the case of the inventive system's use in a plasma environment, the system is preferably mounted about 6 inches or more away from the plasma zone in order to minimize the formation of deposits on the windows and other cell surfaces.

Because the detection system described above can be used in plasma or non-plasma atmospheres as well as with inert or reactive gases, the system is particularly well suited for use in monitoring gas phase molecular species, such as water vapor, in a semiconductor processing apparatus. Use of the detection system in conjunction with a semiconductor processing apparatus allows for real time in-situ monitoring of gas phase molecular impurities.

The system can be readily adapted to virtually any semiconductor processing apparatus which involves exhausting of a process chamber, for example, by employing a vacuum system. Examples of such apparatuses include etching, diffusion, chemical vapor deposition (CVD), ion implantation, sputtering and rapid thermal processing apparatuses.

Figure 8:
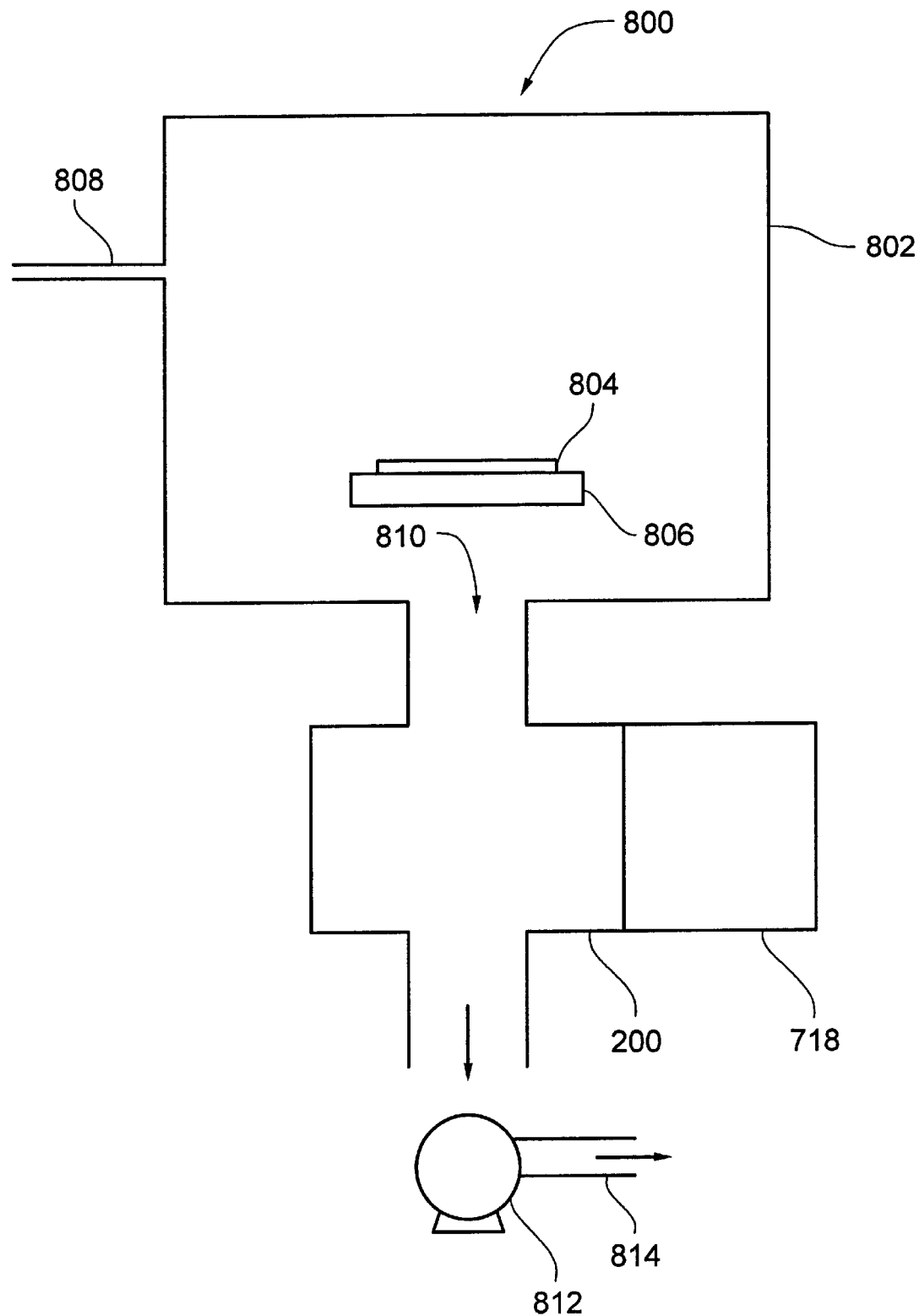
FIG. 8 is a side sectional view of a semiconductor processing apparatus which includes a system for performing an absorption spectroscopy measurement in accordance with the invention.

FIG. 8 illustrates a semiconductor processing system 800 which comprises an in-line cell and system for performing absorption spectroscopy measurements as described in detail above. The system further includes a processing chamber 802, e.g., a vacuum chamber, inside which a semiconductor substrate 804 is disposed on a substrate holder 806. One or more gas inlets 808 are provided for delivering a gas or plural gases to the processing chamber.

The processing chamber is evacuated through an exhaust opening 810 in the vacuum chamber. A portion of the total exhaust from the processing tool or the entire exhaust volume can be introduced into cell 200. A vacuum pump 812 for evacuating the vacuum chamber is connected thereto, either directly or through a vacuum line. A pump exhaust line 814 can be connected to the pump 812, which can be connected to another pump or to a gas scrubber (not shown). Examples of vacuum pumps which may be employed are mechanical rotary and booster pumps, diffusion pumps, cryogenic pumps, sorption pumps and turbomolecular pumps. It is not, however, necessary that the processing chamber be evacuated by a vacuum pump. For example, evacuation of the chamber through the measurement cell can be by a blower or scrubber alone. Such a configuration is commonly used, for example, in atmospheric pressure CVD systems.

Furthermore, while the vacuum pump and measurement system have been illustrated as being disposed below the vacuum chamber, those skilled in the art readily understand that other orientations are also possible.

While the invention has been described in detail with reference to specific embodiments thereof, it will be apparent to one skilled in the art that various changes and modifications can be made, and equivalents employed, without departing from the scope of the appended claims.

What is claimed is:

1. An in-line cell useful in absorption spectroscopy, comprising a sample region, a light entry port and a light exit port being the same or separate ports, each said port being in communication with the sample region and containing a light transmissive window, a mirror having a light reflective surface facing the sample region and a heater effective to heat said light transmissive window in said light entry port and/or said light exit port, wherein the thermal resistance of a path from the heater to the light transmissive window being heated is less than the thermal resistance of a path from the heater to other surfaces of the sample cell.

2. The in-line cell according to claim 1, wherein the heater is disposed outside of the cell.

3. The in-line cell according to claim 2, wherein the heater is in direct contact with a back surface of the light transmissive window being heated.

4. The in-line cell according to claim 1, wherein the heater is a resistance-type heater.

5. The in-line cell according to claim 1, wherein the cell is a multipass cell.

6. The in-line cell according to claim 1, further comprising a purge gas inlet effective to introduce a purge gas stream which contacts the heated light transmissive window.

7. The in-line cell according to claim 1, wherein the light transmissive window in the light entry port is offset from perpendicular with respect to an incoming light beam.

8. The in-line cell according to claim 1, further comprising an additional heater effective to heat the light reflective surface of the mirror.

9. The in-line cell according to claim 1, wherein the light transmissive window and the light reflective surface are integrated into a wall of the cell.

10. A system for performing an absorption spectroscopy measurement, comprising:
   a sample region, a light entry port and a light exit port being the same or separate ports, each said port being in communication with the sample region and containing a light transmissive window, a mirror having a light reflective surface facing the sample region, and a heater effective to heat said light transmissive window in said light entry port and/or said light exit port, wherein the thermal resistance of a path from the heater to the light transmissive window being heated is less than the thermal resistance of a path from the heater to other surfaces of the sample cell,
   a light source for generating a light beam which passes through the light entry port into the cell, and a main detector for measuring the light beam exiting the cell through the light exit port.

11. The in-line cell according to claim 10, wherein the heater is disposed outside of the cell.

12. The in-line cell according to claim 11, wherein the heater is in direct contact with a back surface of the light transmissive window being heated.

13. The system according to claim 10, wherein the heater is selected from the group consisting of resistance-type heaters, self-regulating-type heaters, heating lamps, inductive heaters and a heating fluid.

14. The system according to claim 10, further comprising a purge gas inlet effective to introduce a purge gas stream which contacts the heated light transmissive window.

15. The in-line cell according to claim 10, further comprising an additional heater effective to heat the light reflective surface of the mirror.

16. The in-line cell according to claim 10, wherein the light transmissive window in the light entry port is offset with respect to an incoming light beam from perpendicular.

17. The system according to claim 10, wherein the cell is disposed between and in communication with a vacuum chamber and a vacuum pump.

18. A semiconductor processing apparatus, comprising:

a processing chamber in communication with a means for evacuating the chamber, an in-line cell disposed between and in communication with the processing chamber and the evacuating means, the cell comprising a sample region, a light entry port and a light exit port being the same or separate ports, each said port being in communication with the sample region and containing a light transmissive window, a mirror having a light reflective surface facing the sample region, and a heater effective to heat said light transmissive window in said light entry port and/or said light exit port, wherein the thermal resistance of a path from the heater to the light transmissive window being heated is less than the thermal resistance of a path from the heater to other surfaces of the sample cell, a light source for generating a light beam which passes through the light entry port into the cell, and a main detector for measuring the light beam exiting the cell through the light exit port.

* * * * *